(12) United States Patent
Fercher (10) Patent No.: US 7,695,137 B2
(45) Date of Patent: Apr. 13, 2010

(54) SHORT-COHERENCE INTERFEROMETRIC MEASUREMENT OF LENGTH ON THE EYE

(75) Inventor: Adolf Friedrich Fercher, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 620 days.

(21) Appl. No.: 10/586,220

(22) PCT Filed: Feb. 4, 2005

(86) PCT No.: PCT/EP2005/001164

§ 371 (c)(1),
(2), (4) Date: Jul. 17, 2006

(87) PCT Pub. No.: WO2005/074789

PCT Pub. Date: Aug. 18, 2005

(65) Prior Publication Data

US 2008/0218691 A1  Sep. 11, 2008

(30) Foreign Application Priority Data

Feb. 6, 2004  (AT) ............................... A 179/2004
Apr. 27, 2004  (AT) ............................... A 719/2004

(51) Int. Cl.
*A61B 3/10* (2006.01)
(52) U.S. Cl. .................... 351/205; 351/236; 351/220
(58) Field of Classification Search .................. 351/205
See application file for complete search history.

(56) References Cited

U.S. PATENT DOCUMENTS 5,847,827 A * 12/1998 Fercher ...................... 356/493
6,053,613 A * 4/2000 Wei et al. .................... 351/205
2002/0041359 A1* 4/2002 Mihashi et al. ............. 351/221
2004/0061830 A1* 4/2004 Hellmuth et al. ........... 351/205

FOREIGN PATENT DOCUMENTS

DE  32 01 801  9/1983

(Continued)

*Primary Examiner*—Jessica T Stultz
(74) *Attorney, Agent, or Firm*—Eugene Ledonne; Joseph W. Treloar; Frommer Lawrence & Haug LLP (57) ABSTRACT

Two problems arise when measuring length at the eye by short-coherence interferometry. First, the measurement focus and coherence window usually do not coincide. Second, the scanning process along the eye axis is time-consuming. Both result in poor signal quality and inaccurate measurements. The present application is directed to a short-coherence interferometer in which a right-angle mirror and focusing optics jointly carry out a periodic back-and-forth movement in such a way that the measurement beam focus which is generated by the focusing optics and imaged on the eye by relay optics is moved synchronously with the coherence window from the cornea along the optic axis of the eye to the fovea centralis. Further, different path lengths are generated in the measurement beam path and reference beam path by means of a plurality of reflectors, so that the scanning process is limited to distances which are smaller than the optical length of the eye. The present invention is advantageously implemented using on a fiber-optic interferometer. According to the invention, the reference interferometer arm and measurement interferometer arm are combined with the arms of a fiber-optic interferometer.

19 Claims, 11 Drawing Sheets

FOREIGN PATENT DOCUMENTS

| | | |
|---|---|---|
| DE | 196 24 167 | 1/1997 |
| WO | 92/19930 | 11/1992 |
| WO | 01/38820 | 5/2001 |
| WO | 02/04884 | 1/2002 |
| WO | 03/086180 | 10/2003 |

* cited by examiner

SHORT-COHERENCE INTERFEROMETRIC MEASUREMENT OF LENGTH ON THE EYE

CROSS-REFERENCE TO RELATED APPLICATIONS

This application claims priority of International Application No. PCT/EP2005/001164, filed Feb. 4, 2005, Austrian Application No. 179/2004, filed Feb. 6, 2004 and Austrian Application No. 719/2004, filed Apr. 27, 2004, the complete disclosures of which are hereby incorporated by reference.

BACKGROUND OF THE INVENTION a) Field of the Invention

The present application is directed to a measurement method for diagnostic opthalmology, particularly measurement arrangements for measuring partial distance lengths at the eye in connection with cataract surgery and refractive eye surgery.

b) Description of the Related Art

In cataract surgery and refractive eye surgery, a determined refractive power of the eye is obtained or achieved through suitable selection of the refractive power of the intraocular lens to be implanted. For this purpose, it is necessary to measure the eye's initial state of refractive power and also, as the case may be, after operating, to measure the final refractive state. Keratometers are used for measuring the corneal curvature, and acoustic or optical length measurement methods are used for determining the axial partial distances of the eye.

At present, it is already very common to determine axial eye length by optical short-coherence interferometry which, compared with the formerly prevalent ultrasound methods, has the advantage of contactless, highly precise operation. In short-coherence interferometry, interference patterns occur only when the object and reference mirror are situated at the same optical distance from the beamsplitter up to the coherence length $l_C$ or, in other words, when the object structure in question is located in the "coherence window." In order to measure distances of object structures using the conventional time-domain method, these object structures are moved into the coherence window successively in time through monitored displacement of a mirror in the reference beam or measurement beam. Therefore, the measuring accuracy is defined by the coherence length $l_C$ of the measurement light bundle which depends not only on wavelength $\lambda$ but also chiefly on its spectral width $\Delta\lambda$ (strictly speaking, the shape of the spectrum also plays a part):

$$l_C \sim \lambda^2/\Delta\lambda. \quad (1)$$

In opthalmologic short-coherence interferometry, the coherence window usually has a length ($=l_C$) of several micrometers.

In contrast to conventional optical short-coherence interferometry in which the reference mirror of the interferometer traverses or "scans" the entire distance to be measured, special methods have been developed for opthalmologic measurement of eye length. In spite of distances at the eye of up to about 30 millimeters, these methods make it possible to measure these distances even in living and, therefore, unstable objects. One of the alternatives for solving this problem in short-coherence interferometric measurement of the distance of unstable structures which are separated in depth is to use the so-called dual-beam method. This method is described in Laid Open Application DE 3201801A1. In this instance, the cornea and the other eye structure, e.g., the fundus, which is separated from the cornea with respect to depth are illuminated by a dual measurement beam. This dual measurement beam is formed by two output beams of a Michelson interferometer having different path lengths. Using a diffractive lens, this measurement beam is focused on the cornea and on the fundus simultaneously. The Michelson interferometer is adjusted to the distance between the cornea and fundus. An interferometer mirror scan distance of a few millimeters is sufficient for this purpose. This adjustment is determined by the interference patterns of short-coherence light which occur in this way. Since only the distance between the cornea and fundus is decisive in this instance, requirements respecting interferometric stability are satisfied in an ideal manner; measurement is not impeded by movements of the eye.

Also, in the method described in Patent Application WO 01/38820A1, the two object areas which are at a distance from one another with respect to depth are illuminated by a dual measurement beam. In this case, another measurement beam is initially reflected out of the measurement beam illuminating the measured object in front of the measured object by means of a beamsplitter and, after traversing an indirect path in which additional refractive optics can also be arranged for focusing, is reflected into the original measurement beam again. This method reduces the interferometer scan distance to a smaller value than the distance to be measured. With correspondingly fast scanning, this method can likewise meet the requirements for interferometric stability.

However, the methods mentioned above have the disadvantage that the measurement light simultaneously illuminates two or more object areas at a distance from one another. The light that is not used for measurement generates unwanted background and noise. Further, it is difficult to implement focusing of the measurement light on the respective measurement location in this way; these problems are severe in particularly when there is a plurality of object areas at a distance from one another. But modern opthalmologic length measurement at the eye requires measurement of more than one length, namely, distances such as the anterior chamber depth, cornea thickness and eye lens thickness in addition to the eye length.

OBJECT AND SUMMARY OF THE INVENTION

Therefore, it is the primary object of the invention to provide short-coherence interferometers for measuring partial distances of the eye which focus the measurement beam on the respective coherence window and which, further, reduce the required interferometer mirror scan distances to distances that are less than the distances that must be measured.

According to the invention, this object is met by a short-coherence interferometer in which a right-angle mirror and focusing optics jointly carry out a periodic back-and-forth movement in such a way that the measurement beam focus which is generated by the focusing optics and imaged on the eye by relay optics is moved synchronously with the coherence window from the cornea along the optic axis of the eye to the fovea centralis, and, further, different path lengths are generated in the measurement beam path and reference beam path by means of a plurality of reflectors.

DESCRIPTION OF THE PREFERRED EMBODIMENTS

Figure 1:
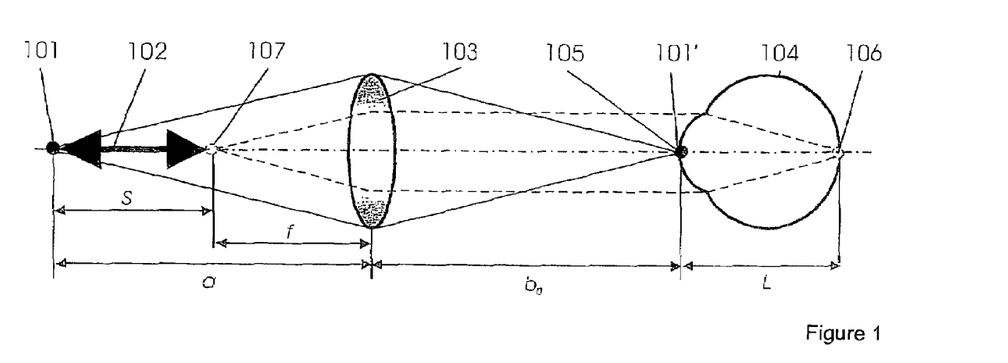
FIG. 1 illustrates in schematic form the geometric optics of the depth scan at the eyes.

FIG. 1 illustrates the geometric optics of the depth scan at the eye: 101 designates the moving focus of the measurement beam of a short-coherence interferometer which moves along the distance of length S indicated by the double-arrow 102. The focus 101 is imaged on the eye 104 by means of relay optics 103. The condition for short-coherence interferometry in this instance is that the image 101' of the focus 101 must scan the entire length of the eye 104 from the corneal vertex 105 to the fovea centralis 106 for a movement of the focus 101 by the optical length S=L of the eye (in Gullstrand's eye model, L is roughly equal to 33 mm). Accordingly, point 107 must be imaged at the end of this movement in point 106. This is achieved for optics with a focal length f when the corneal vertex is situated at a distance of $$b_0 = \frac{f(f+L)}{L} \quad (2)$$

from the relay optics 103. For example, when using optics with a focal length f=33 nun, b=66 mm in Gullstrand's eye model.

Further, the measurement beam must be focused inside the coherence window on the object for a good short-coherence interferometric signal. While the arrangement described in FIG. 1 ensures that when the coherence window at the cornea coincides with the focus 101' it also coincides at the fovea centralis with the focus of the measurement beam in point 106, this is not completely guaranteed along the intervening distance. This can be seen by following the course of the focus position from the corneal vertex 201 (FIG. 2) into the interior of the eye. Because of the refraction of light at the cornea 211, the focus of a light bundle 212 focused on a point 210 behind the cornea 211 is displaced by a shorter distance (t) than the light bundle itself ( ) and therefore than the coherence window. The new focus does not lie in point 210 but rather in 213, see FIG. 2. Further, the coherence window does not lie at 210, but rather at optical distance $n_G \cdot T$ from the vertex, where $n_G$=group index.

Figure 2:
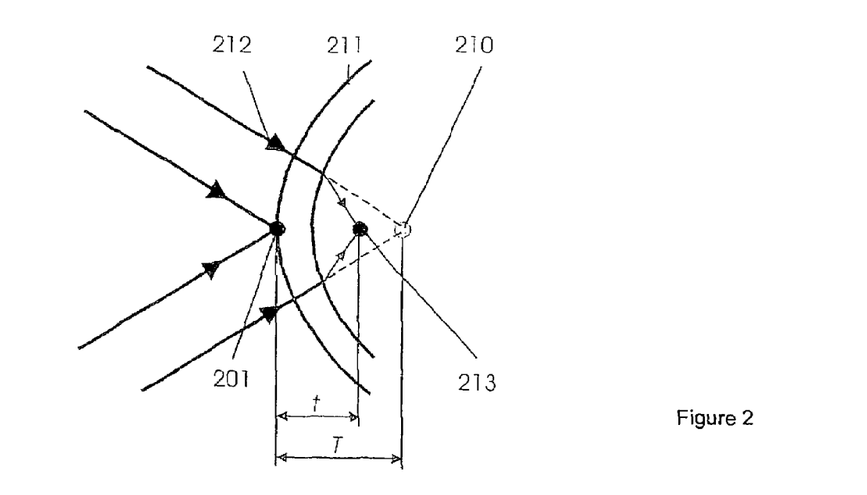
FIG. 2 illustrates in schematic form the course of the focus position from the corneal vertex into the interior of the eye.

This divergence of the coherence window and measurement bundle focus is important particular when taking measurements in the anterior segment of the eye because the latter contains structures (back of the cornea, front and back of the eye lens) that should be measured with high precision. This divergence can be reduced for the anterior segment of the eye by ensuring the initial coincidence of the focus 210 and coherence window not—as is customary—for points outside of the eye, that is, e.g., for the corneal vertex, but for a point approximately in the center of the anterior chamber, e.g., 3 mm behind the vertex. This is achieved by a corresponding positioning of the reflector for the coherence window of the cornea. For this purpose, the arm length of the interferometer is adjusted by means of the adjusting table 358, 558, or 758.

Figure 3:
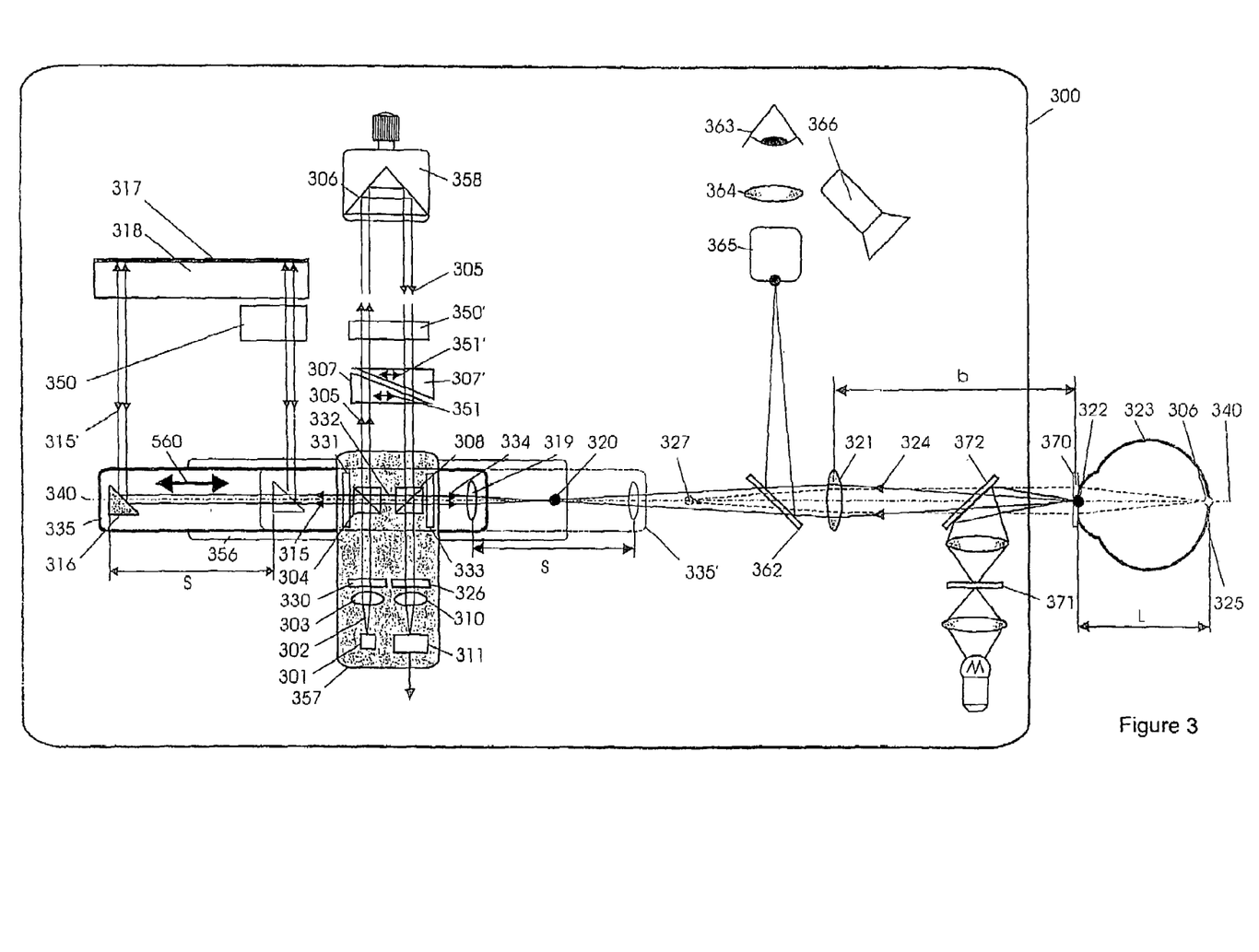
FIG. 3 illustrates in schematic form a first arrangement of the present invention.

A first arrangement according to the invention is shown in FIG. 3. In this instance, a short-coherence light source 301, for example, a superluminescent diode, delivers a light beam 302 which is partially coherent temporally and, as far as possible, fully coherent spatially and which illuminates the beamsplitter 304 by means of optics 303. The beamsplitter 304 divides the light beam 302 into measurement beam 315 and reference beam 305. The reference beam 305 is reflected in direction of the beamsplitter 308 by the reference mirror 306. In this way, it passes through the two dispersion compensation prisms 307 and 307' two times. After passing through the beamsplitter 308, the reference beam 305 strikes the optics 310 and is focused on the photodetector 311 by the latter.

The measurement beam 315 reflected by the beamsplitter 304 (at left in the drawing) is reflected by the right-angle mirror 316 by 90° out of its original direction and strikes the reflector mirror 317 which is formed in this instance as a mirrored rear surface of a plane plate 318'. Of course, other mirrors can also be used for this purpose, for example, surface mirrors with the reflector side facing the incident beam. The reflected measurement beam 315' is directed again to the beamsplitter 304 by the right-angle mirror 316, passes through the beamsplitter 304 and also beamsplitter 308 in a straight line and is focused by the focusing optics 319 as a measurement beam 334 in the focus 320. As is shown in FIG. 3, for example, the focus 320 is located at twice the object-side focal length of the relay optics 321. The relay optics 321 image the focus 320 on the eye 323. As is shown in FIG. 3, for example, the focus 320 is imaged at twice the image-side focal length of the relay optics 321 in point 322. Point 322 is located on the cornea of an eye 323 whose length L is measured.

The beamsplitters 304 and 308 can be constructed as polarizing beamsplitters to prevent unwanted reflections and to optimize the beam intensities. By rotating a linear polarizer 330, the splitting ratio of the reference beam intensity to the measurement beam intensity can then be optimized in such a way that an optimal signal-to-noise ratio is obtained at the photodetector 311. Further, a quarter-wave plate 331 can be arranged after the beamsplitter 304 in the measurement beam 315 at 45° to the polarization direction. The reflector 317 is then illuminated by a circularly polarized light bundle 315 which is circularly polarized in the opposite direction after reflection as light bundle 315' and then, after a further pass through the quarter-wave plate 331, is linearly polarized again, namely, orthogonal to the original polarization direction. This beam 332 therefore traverses the polarizing beamsplitters 304 and 308 without reflection losses and strikes another quarter-wave plate 33 arranged at 45°, where the measurement beam 334 is circularly polarized again and is focused by the focusing optics 319 in focus 320 and again, by the relay optics 321, in focus 322. The corneal vertex reflects the light bundle 324 which is now circularly polarized in the opposite direction. This returning measurement light bundle 324 is again linearly polarized orthogonal to the polarization direction of the bundle 332 by the quarter-wave plate 333 and is therefore reflected by 100% in direction of the optics 310 by the polarizing beamsplitter 308 and is focused by the latter on the photodetector 311. In this way, output losses in the measurement beam are prevented to a great degree.

After being reflected at the reference reflection prism 306, the linearly polarized reference beam 305 traverses the dispersion compensators 307 and 307' and the beamsplitter 308 and is likewise focused on the photodetector 311 by the optics 310. The size of the mutually interfering components from the measurement beam and reference beam can be adjusted by the linear polarizer 326. The linear polarizer 326 is oriented in such a way that an optimal signal-to-noise ratio occurs at the photodetector 311.

The short-coherence interferometer described above is constructed on a plate 300. The right-angle mirror 316 and focusing optics 319 are located on a scanner plate 335 (335') which is movable in direction of the interferometer axis 340, shown in dash-dot lines, by distance S. The scanner plate 335 can be the moving slide of a voice coil scanner, e.g., manufactured by the firm Physik Instrumente, or of an ultrasound scanning table or other corresponding device whose base plate 356 is fastened to the bottom plate 300. On the other hand, components 301, 302, 303, 304, 331, 308, 333, 326, 310, and 311 are located on a carrier plate 357 which is fixedly connected to the bottom plate 300 and spans the scanner plate 335.

The reflection prism 306 is mounted on a displacement table 358. Its position can be adapted in such a way that the coherence window is located at the corneal vertex of the eye 323 in the configuration of the scanner plate 335 of the interferometer indicated in FIG. 3 by solid lines. When the scanner plate 335—on which the right-angle mirror 316 and focusing optics 319 are mounted—moves in direction of the interferometer axis 340, shown in dash-dot lines, by distance S, the measurement beam path to the left of the beamsplitter 304 in the drawing is reduced by 2 times S. As a result, the coherence window is displaced by distance S from the corneal vertex into the eye. In order to measure eye length, the coherence window can be displaced to the right by the entire optical eye length L, and this distance can be delimited based on the short-coherence interference patterns that occurs between the light reflected by the fondus 325 and the reference light. Alternatively, as was stated above, the position of the reflection prism 306 can be adapted in such a way by means of the displacement table 358 that the focus for a point roughly in the center of the anterior chamber of the eye is situated in the middle of the coherence window. An adjustment of this kind is particularly important when precise measurements of the anterior chamber geometry must be carried out.

The accuracy of short-coherence interferometric measurements is impaired by dispersion in the interferometer arms. To achieve the greatest possible accuracy which is approximately on the order of the coherence length $l_C$, the dispersion in the two interferometer arms must be identical as far as possible. This is referred to as dispersion compensation. The dispersion caused by the component parts of the interferometer can be achieved by correspondingly selected thicknesses of the mirror plate 318 or by additional plane plates (350, 350'). The object-dependent dispersion can be compensated in the reference arm by mutual displacement (double-arrows 351 and 351') of two wedge plates (307, 307').

A semitransparent mirror 362 can be arranged in the measurement beam in order to observe the position of the test subject's eye 323 relative to the measurement beam. This observation can be carried out directly (363), by means of an eyepiece 364, or by means of a television camera 365. For this purpose, it may be advisable to additionally illuminate the test subject's eye 323 with an incoherent light source 366. The image 370 of a reticle 371 reflected on the test subject's cornea by a semitransparent mirror 372 can also be used for precise positioning of the test subject's eye on the interferometer axis 340.

The methods described above have the disadvantage that the scanner plate 335 must be displaced by the entire eye length L, which is time-consuming.

Figure 4:
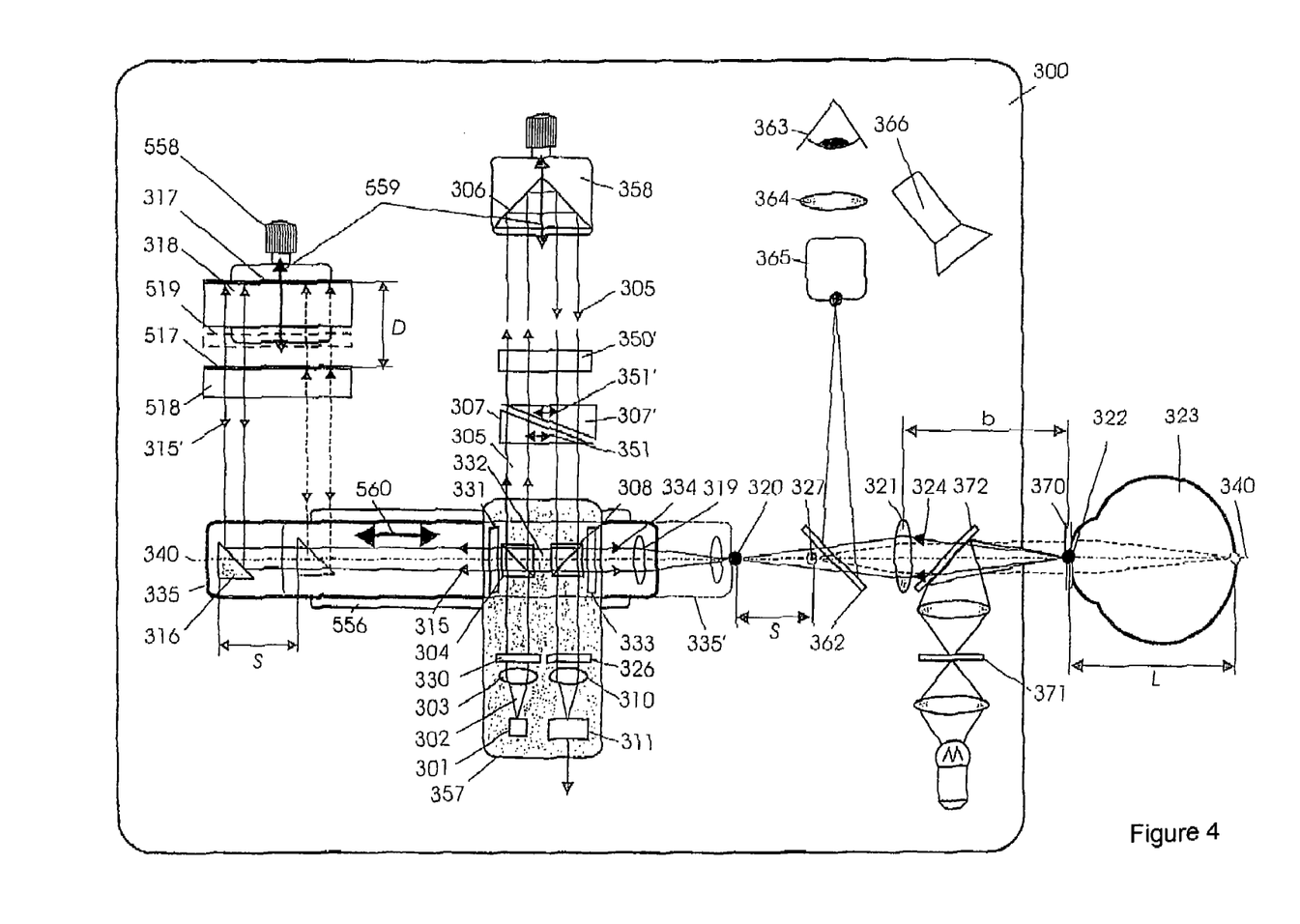
FIG. 4 illustrates in schematic form a second arrangement of the present invention.

In another construction of the invention, another reflector 517 is arranged in front of reflector 317 as is shown in FIG. 4. This plane mirror is located at a known distance D from the reflector 317. A portion of the measurement light beam 315 is already reflected at this mirror. This portion of the measurement light beam 315' already has a coherence window that is offset toward the right-hand side by the optical length D relative to the measurement light reflected at the reflector 317. When the interferometer has been adjusted in such a way that the measurement light reflected by the reflector 317 (associated with the cornea) generates short-coherence interference with the reference light after reflection at the cornea, a displacement of the scanner plate 335 by distance S=L−D is already sufficient to allow short-coherence interference between the light bundle that is directed to the ocular fundus from the reflector 517 (associated with the fundus) and reflected thereat and the reference light. The eye length L is given by the distance L−D measured by short-coherence interferometry and the known distance D. The distance between the corneal vertex and the relay optics 321 must then equal $$b = f + \frac{f^2}{L-D} \qquad (3)$$

The modifications described in relation to the arrangement according to FIG. 3 for preventing unwanted reflections, for dispersion compensation, and for observation of the position of the test subject's eye can also be implemented in the beam path according to FIG. 4 in an analogous manner. Further, the position of the reflector 317 and the roof prism 306 can be adapted to the actual partial length distances of the eye by means of the displacement table 558 and 358 through axial displacement (double-arrow 559) in such a way that the required mechanical scan process is reduced to a few millimeters by the scanner plate 335 of the short-coherence interferometer. Accordingly, not only is the measurement process at the eye made considerably faster, but the use of inexpensive scanners is also made possible.

Further, in addition to eye length, the different intraocular partial distances can also be measured. For this purpose, additional reflectors can be arranged so as to be staggered with respect to depth, e.g., a reflector 519, so that its position roughly corresponds to the position of the front surface of the lens. The distance between the cornea and eye lens can then also be measured based on corresponding short-coherence interference.

The thickness of the carrier plates of the reflectors (318, 518, 519) can be adapted in a corresponding manner to the required dispersion compensation.

In the arrangements described thus far, all of the measurement beams associated with the different object depths are still at the photodetector simultaneously because the reflectors 517 and 519 must be semitransparent. This reduces the signal quality and can lead to confusion between signals. This problem is prevented by the further development of the arrangement according to the invention which is described in the following.

Figure 5:
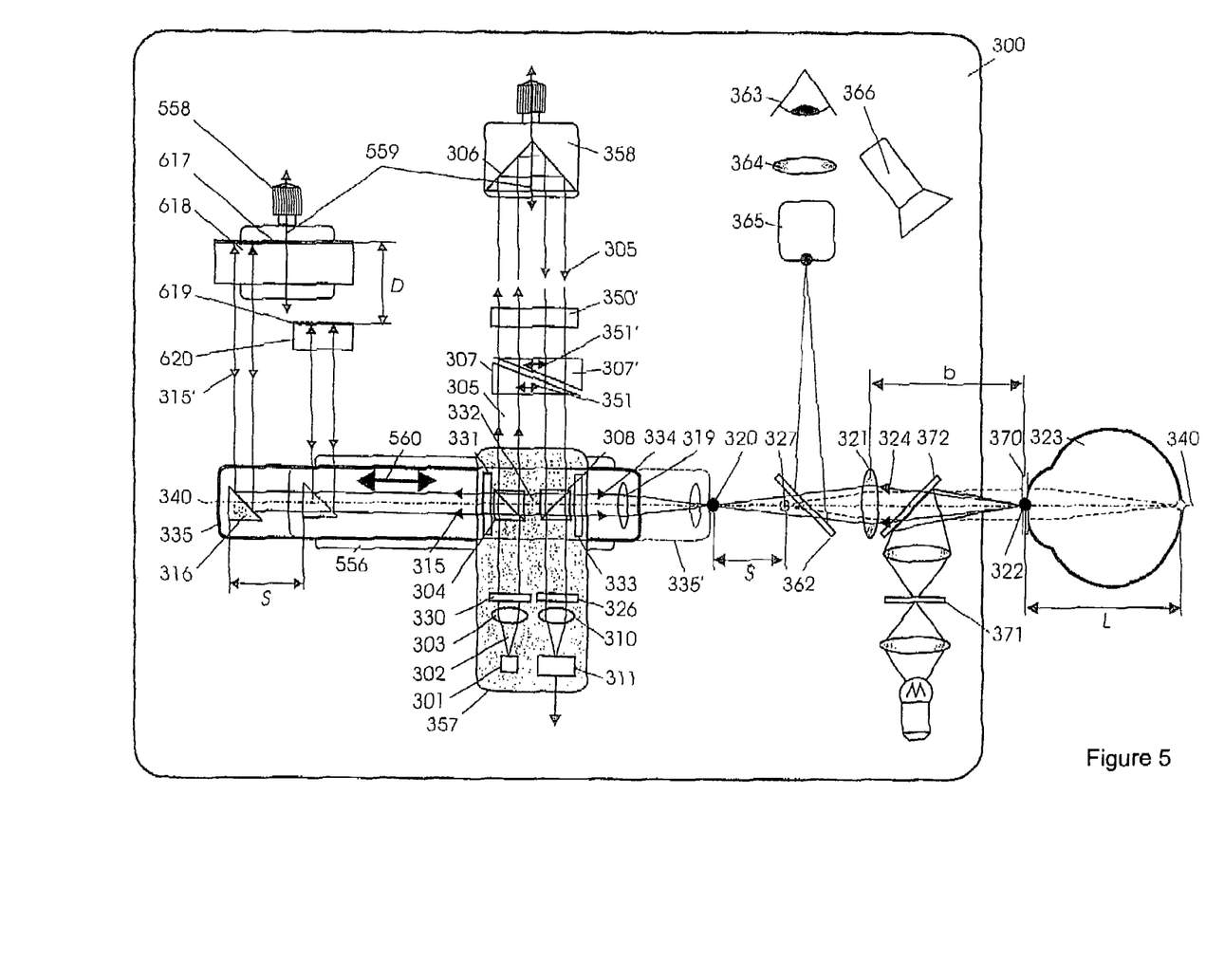
FIG. 5 illustrates in schematic form a third arrangement of the present invention.

In the arrangement according to FIG. 5, depending upon the position of the scanner plate 335, the measurement beam 315 which is reflected by 90° from its original direction by the right-angle mirror 316 impinges on a plurality of reflectors 617 (with plate 618) and 619 (with plate 620) which are staggered not only in depth but also laterally. As a result, only one measurement beam takes part in the short-coherence interferometric measurement. In this instance, all reflectors can be fully mirrored. All of the measurements that are separated with respect to depth are now carried out separately optically. Also, the scanner plate 335 need only be moved by a distance of about S=L−D for measuring the eye length L. Here also, the distance of the corneal vertex from the relay optics 321 must equal $$b = f + \frac{f^2}{L - D}.$$

Figure 6:
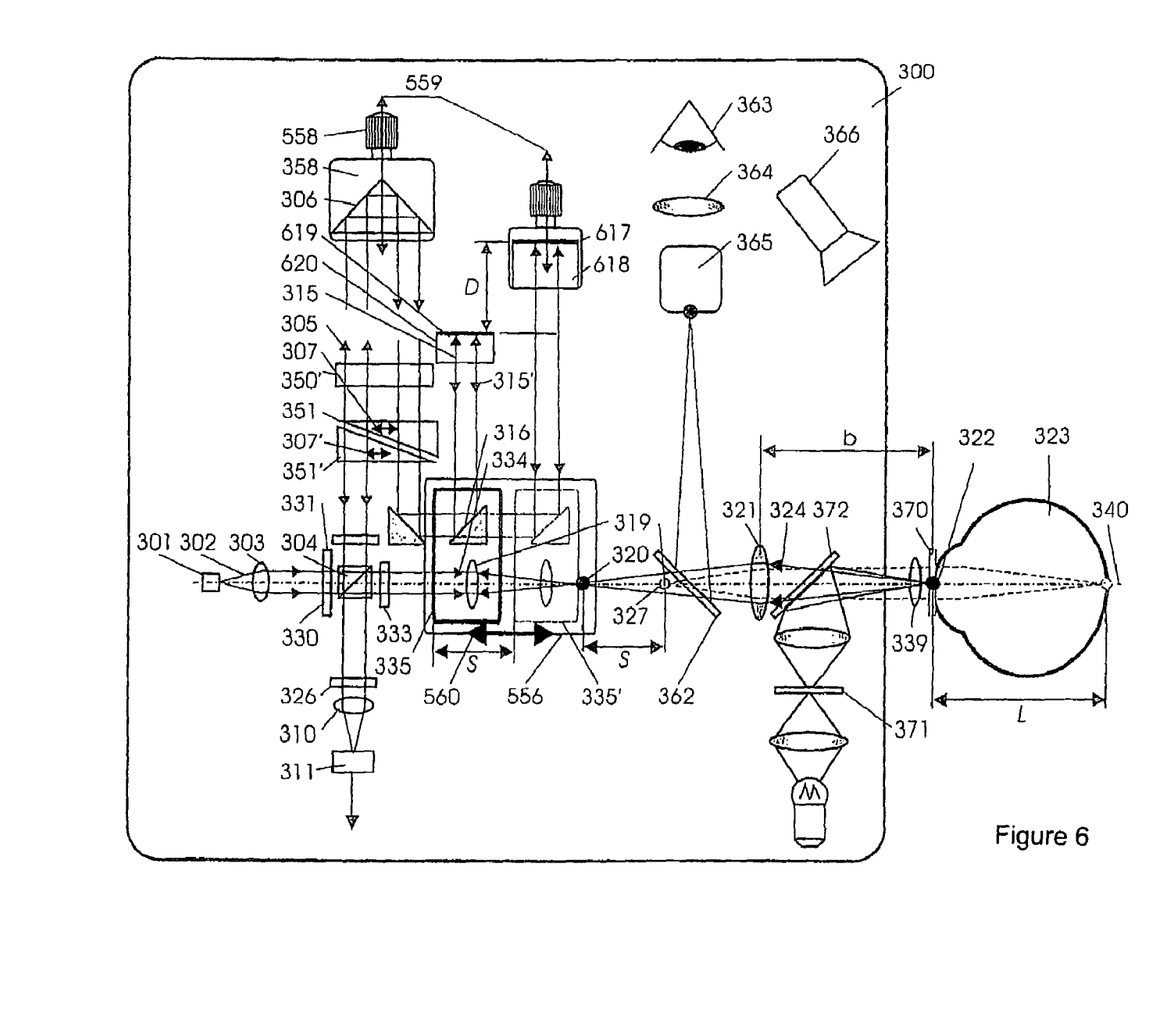
FIG. 6 illustrates in schematic form a simplified interferometer construction in accordance with the present invention.

FIG. 6 shows a simplified interferometer construction. In this instance, the right-angle mirror 316 and focusing optics 319 are mounted next to one another on the scanner plate 335 which is moved back and forth (double-arrow 560) periodically in direction of the optical axis 340 between the position 335 shown in solid lines and the position 355' shown in dashed lines. The rest of the reference numbers correspond to those in the preceding drawings. In this instance, the carrier plate 357 is not required.

Also, all of the other devices discussed with reference to FIGS. 3, 4 and 5, e.g., for preventing unwanted reflections by polarization-optical steps and the dispersion compensation, can be carried out for the arrangement according to FIG. 6. In case of defective vision, collecting or dispersive auxiliary optics 339 for compensating defective vision can be placed in front of the eye 323.

Figure 7:
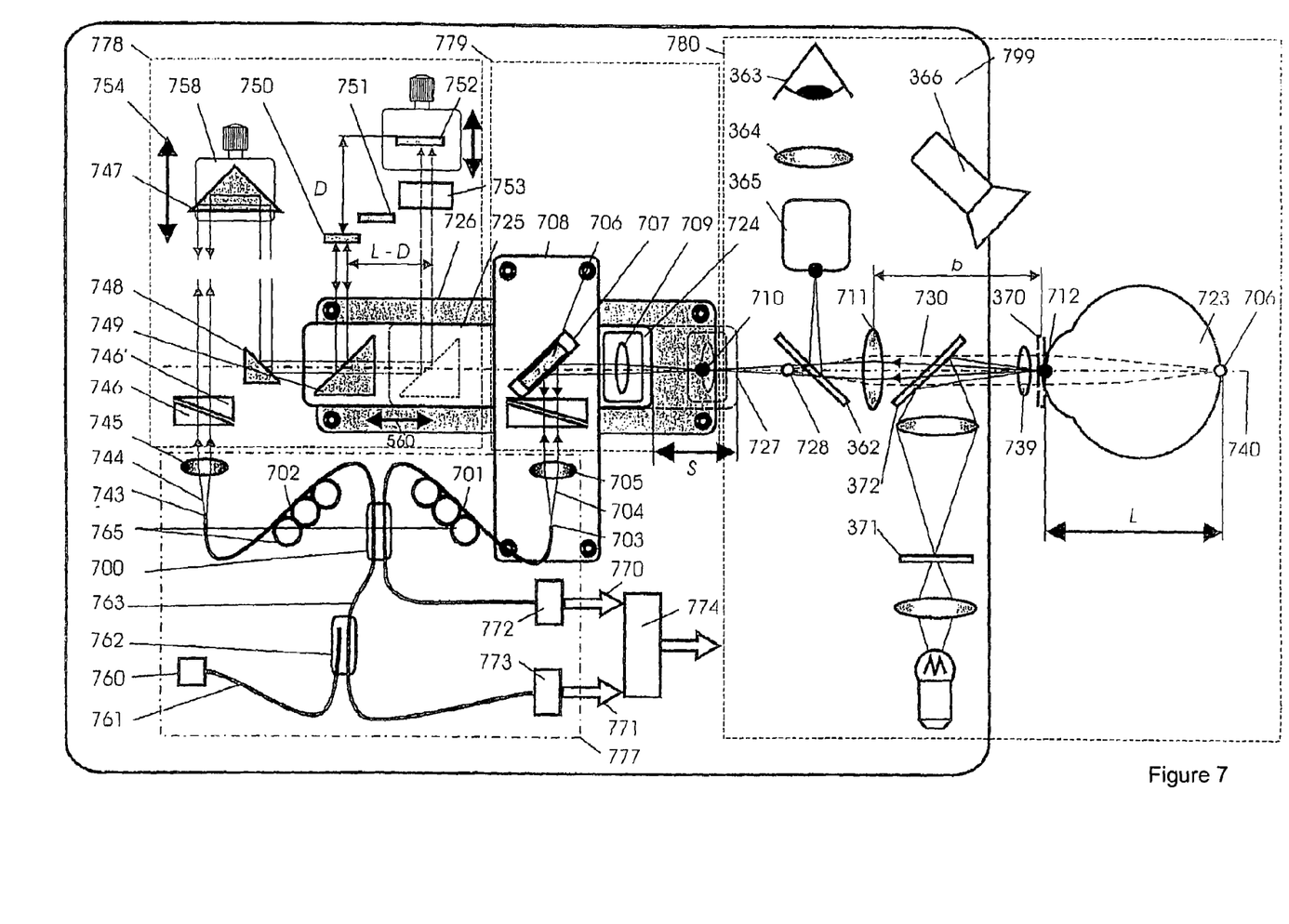
FIG. 7 shows an example in schematic form of a specific arrangement of the system shown in FIG. 4.

With regard to fiber-optic implementation of the arrangements according to the invention, an advantageous implementation of the present invention is carried out based on a fiber-optic interferometer. A reference interferometer arm and measurement interferometer arm which are designed in accordance with the invention are combined with the arms of a fiber-optic Michelson interferometer. Advantages result because the central interferometer structure with the fiber-optic beamsplitters is compact, stable against vibrations, and operates reliably. There are various ways to design the fiber-optic Michelson interferometer particularly on the detector side. FIG. 7 shows (in the box 777 in dash-dot lines) a fiber-optic interferometer with balanced detection according to the prior art. Balanced detection compensates for mode noise in the broadband light sources that are required for this purpose, which enables a signal-to-noise gain of up to 20 dB. The invention is not directed to this fiber-optic interferometer or to the associated signal processing. Other fiber-optic interferometers can also be used, for example, those employing fiber-optic circulators. Rather, the invention is directed to the opto-mechanical structure and implementation of the optical beam paths coupled to the fiber interferometer outputs 703 and 743. Outputs 703 and 743 can use different fiber-optic interferometers. Also, the signal processing can be carried out in different ways. For example, the electric output signal can reproduce the direct time sequence of the interference term or it can be demodulated so that only the envelope appears at the output.

Essential to the fiber-optic Michelson interferometer is a fiber coupler 700 which distributes the light coming from the short-coherence light source 760 to the interferometer measurement arm 701 and the interferometer reference arm 702. The light bundle 704 exiting the fiber at 703 is collimated by the optics 705 of a fiber collimator and is directed by the mirror 706 in direction of the optical axis 740 of the short-coherence interferometer. To facilitate adjustment, the reflector 706 is mounted in a holder 707 which is rotatable around two axes lying in its mirror plane. The holder 707 is fixedly mounted on the plate 708 which is in turn fixedly connected to the bottom plate 799 and spans the scanner plate 725. The light bundle 704 reflected by the mirror 706 in direction of the optical axis 740 is focused by the focusing optics 709 in the focus 710. The focus 710 is imaged by the relay optics 711 in point 712. The point 712 is located on the cornea of an eye 723 whose length L is measured.

The focusing optics 709 are mounted on the scanner plate 725 by means of a holder 724. The scanner plate 725 can be the moving slide of a voice coil scanner, e.g., manufactured by the firm Physik Instrumente, or of an ultrasound scanning table or other corresponding device whose base plate 726 is fastened to the bottom plate 799. During the measurement, the scanner plate 725 is moved back and forth periodically along the optical axis 740 by distance S between the position 725 shown in continuous lines and the position 727 shown in dashed lines. When the scanner plate is located in the position shown in dashed lines, the focus of the light bundle 704—for example, in the configuration shown in FIG. 7—is in focal point 728 of the relay optics 711, and the light bundle 35 is directed to the eye 723 as a parallel collimated light bundle 730. The eye focuses this light bundle on its fundus. In case of defective vision, collecting or dispersive auxiliary optics 739 for compensating defective vision can be placed in front of the eye 723.

The reference light bundle 744 exiting at 743 from the light-conducting fiber 702 is collimated by the optics 745 of a fiber collimator and, after passing a dispersion compensation device comprising, for example, two wedge plates (746, 746'), is directed by the roof mirror 747 to the right-angle mirror 748 and from the latter in direction of the optical axis 740 of the short-coherence interferometer. The light bundle 744 strikes the moving right-angle mirror 749 which directs the light bundle 744 to the reflector 750. The reference light bundle 744 is reflected by this mirror in itself and travels back into the light fiber 702.

When the scanner plate 725 moves along the optical axis 740 in direction of the position shown in dashed lines, the reference light bundle 744 is directed to the reflectors 750, 751 and 752 successively by the right-angle mirror 749. Additional reflectors can be arranged in a staggered manner with respect to depth and laterally. Further, plane plates 753 can also be arranged for dispersion compensation. Accordingly, reference light distances of different lengths are realized, for example, in order to measure positions of other structures such as the inner corneal surface, the front surface of the lens, and the back surface of the lens in addition to the position of the fundus and corneal vertex.

FIG. 7 shows an example in which the distance between the reflectors 750 and 752 (which are associated with the cornea and fundus) is equal to distance D. As was already described in connection with the arrangement according to FIG. 4, the distance to be traveled by the scanner plate 725 for measuring eye length is reduced by D. Only a movement by distance S=L−D is required for measuring the length L of an eye. In fact, this distance could even be close to zero: the scanner plate 725 would actually only have to be moved by the coherence length $l_C$ in order to detect the interference. However, because of the scattering of actual eye lengths, which is quite extensive, the scanner plate 725 would have to be moved by a distance approximately equal to this scattering, that is, by several (x) millimeters. In any case, the distance L to be scanned, which is otherwise quite long, can be reduced to a few millimeters. The reflectors 750, 751, 752 must be correspondingly wide, namely, equal to the width of the beam 744 plus x millimeters. Further adaptation is possible by adjusting the reference beam length by means of the reflection prism 747 which is mounted on an adjusting device 758 which is displaceable in the directions indicated by the double-arrows 754.

According to the invention, as is indicated above, the measurement light bundle 704 in the positions 625 and 727 of the scanner plate is focused once on the cornea and once on the fundus. As was already mentioned with reference to FIG. 3, in order that the measurement beam 704 is focused once on the cornea (scanner plate position indicated by solid lines) and once at the other end of the movement (scanner position indicated by dashed lines), the distance of the vertex of the front surface of the cornea from the relay optics 711 must be equal to $$b = f\left(1 + \frac{f}{L-D}\right),$$

where f is the focal length of the relay optics 711. In case the coherence window is initially (scanner plate position 725) situated at the cornea, it will be situated at the fundus at the conclusion of the displacement of the scanner plate (scanner plate position 727). For example, when S=f then b=2f, for a focal length of the relay optics 711 of f=50 mm, then b=100 mm.

It should be mentioned that the actual mechanical scan area for the scanner plate 725 is selected so as to be somewhat larger than S, for example, in order to achieve an approximately constant speed in the actual measurement area, which facilitates the subsequent electronic signal processing.

Further, the position of the reflection prism 747 can be adapted by means of the displacement table 758 in such a way that the focus of the measurement beam on the eye for a point approximately in the center of the anterior chamber also lies in the center of the coherence window. An adjustment of this kind is particularly important when the anterior chamber geometry must be precisely measured.

In this instance, as was already mentioned in connection with the reflector 519 in FIG. 4, the anterior chamber depth, for example, or other partial distances of the eye can also be measured by means of an additional reflector 751.

A superluminescent diode or other short-coherence light source outfitted with a pigtail fiber can be used as short-coherence light source 760. Its radiation must be coupled into the light-conducting fiber 761 by couplers corresponding to the prior art. When using a pigtail superluminescent diode, the radiation can be coupled directly from the pigtail into the first fiber coupler 762. This fiber coupler 762 couples the light wave into the fiber 763 which distributes the light wave in the 50:50 coupler (3 dB coupler) 700 to measurement fiber 701 and reference light fiber 702. Fiber-loop polarization controllers 765 can be used to adjust the polarization state in the two interferometer arms. The electric outputs 770 and 771 of the two photodetectors 772 and 773 are applied to the inputs of a differential amplifier 774 whose output signal is bandpass-filtered and demodulated, for example.

As was already mentioned in connection with the arrangement described with reference to FIG. 3, a semitransparent mirror 362 can also be arranged in the measurement beam in this instance in order to observe the position of the test subject's eye 723 relative to the measurement beam. Observation can then be carried out directly (363), by means of an eye-piece 364, or by means of a television camera 365. In this instance, it can also be useful to additionally illuminate the test subject's eye 323 by an incoherent light source 366. Further, the image 370 of a reticle 371 which is reflected on the test subject's cornea by a semitransparent mirror 372 can also be used for precise positioning of the test subject's eye on the interferometer axis 740.

Three boxes 778, 779 and 780 (in dashed lines) are shown in FIG. 7. The components in these boxes form functional groups which can be set up separately to a great extent. The beam path indicated in FIG. 8 differs from that shown in FIG. 7 first in that the moving right-angle mirror 749 associated with the reference beam path and the focusing optics 709 generating the focus 710 in the measurement beam path are arranged next to one another on the scanner plate. Accordingly, the plate 708 is dispensed with, and all of the components located thereon can be mounted directly on the bottom plate 799, which not only simplifies the construction in its entirety, but also makes it more stable.

Figure 9:
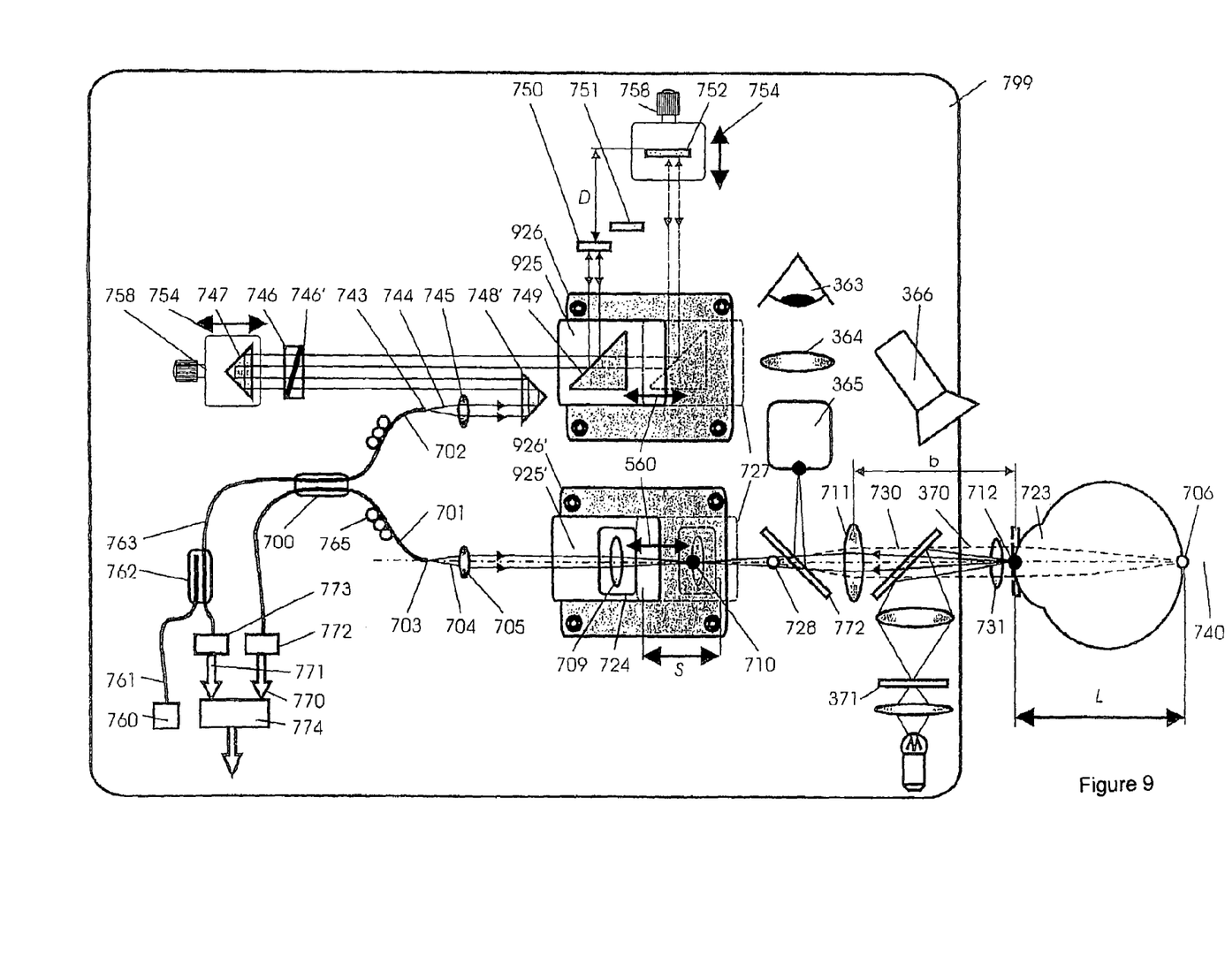
FIG. 9 shows another beam path according to the invention in which the moving right-angle mirror of the interferometer reference arm and the moving focusing optics of the interferometer measurement arm are mounted on separate scanner plates.

Finally, FIG. 9 shows another beam path according to the invention in which the moving right-angle mirror 749 of the interferometer reference arm and the moving focusing optics 709 of the interferometer measurement arm are mounted on separate scanner plates 925 and 925'. These separate scanner plates can be electrically synchronized. However, they can also be operated with different scanning distances. It need only be ensured that S≧L−D and the distance of the vertex of the front surface of the cornea from the relay optics 711 equals $$b = f\left(1 + \frac{f}{L-D}\right),$$

where f is the focal length of the relay optics 711. With the parameters otherwise remaining the same, the opthalmologic short-coherence interferometer can easily be fitted to other ophthalmologic devices and measurement devices through suitable selection of the focal length f of the relay optics 711. Instead of the interferometer reference arm shown here, a so-called rapid scan optical delay line, as is described in K. F. Kwong, et al., 400-Hz mechanical scanning optical delay line, Optics Letters 18 (1993) pp. 558-560, can be combined, as reference arm, with the interferometer measurement arm according to FIG. 9.

Figure 8:
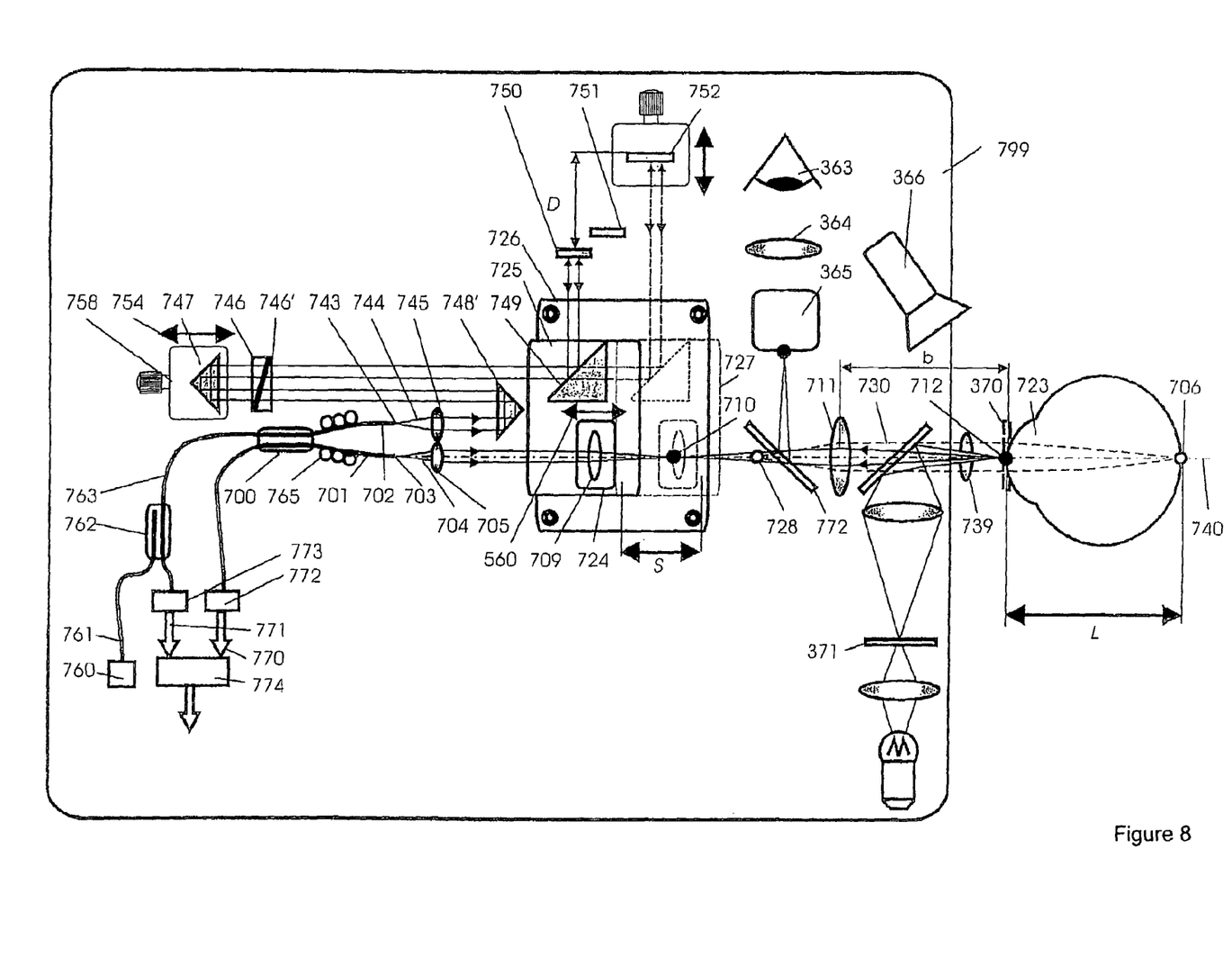
FIG. 8 shows an arrangement in schematic form in accordance with the invention where the beam path differs from that shown in FIG. 7.

The modifications described in connection with the arrangement shown in FIG. 3 for preventing unwanted reflections, for dispersion compensation, and for observation of the position of the test subject's eye can also be realized in an analogous manner in the beam path according to FIGS. 7, 8 and 9. Further, using the displacement table 758, the position of the reflector 752 and the roof prism 747 can be adapted by axial displacement (double-arrow 754) to the actual partial distance lengths of the eye in such a way that the required mechanical scan process of the short-coherence interferometer is reduced to a few millimeters. This not only makes the measurement process at the eye considerably faster, but also make it possible to use inexpensive scanners.

Figure 10:
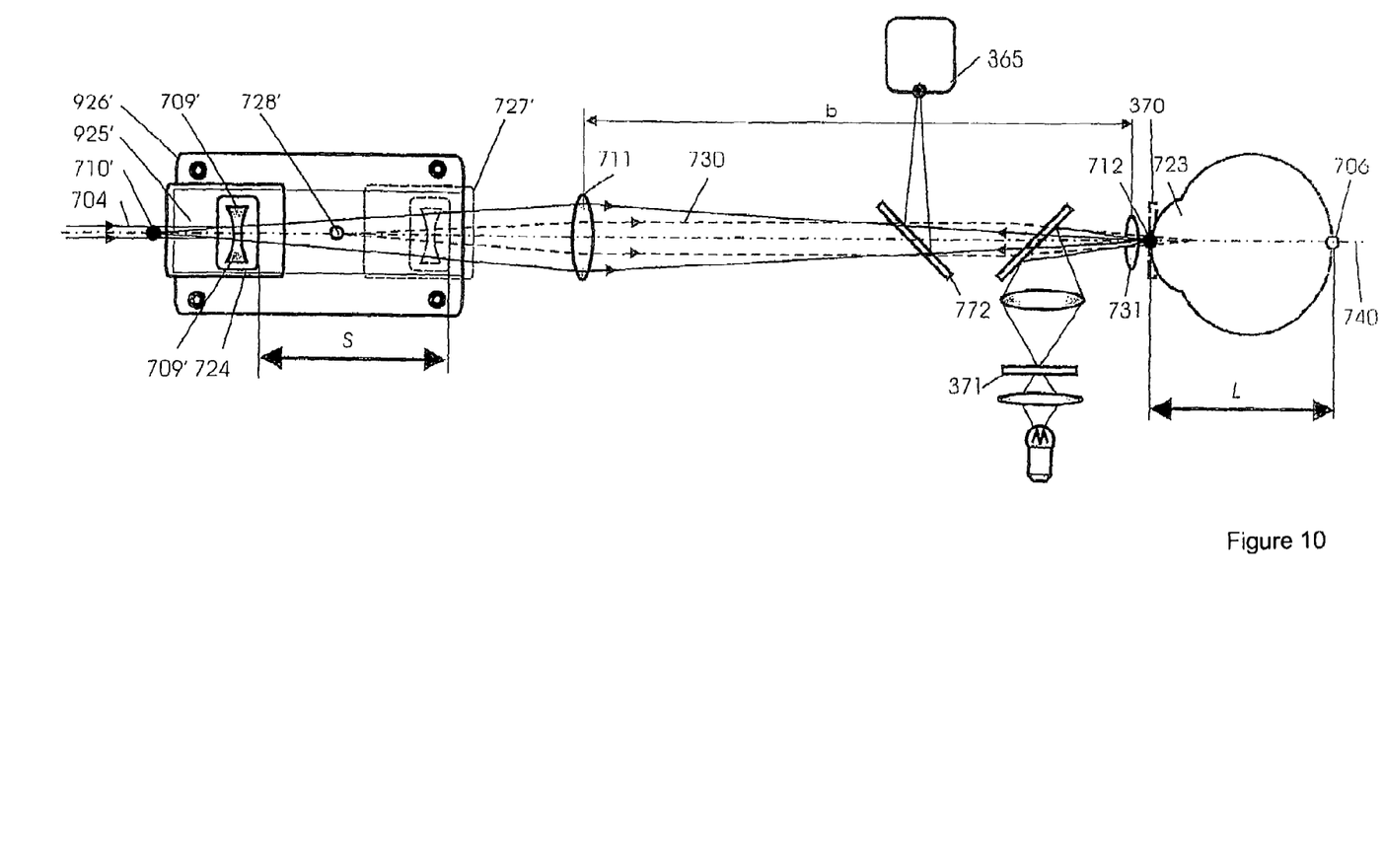
FIG. 10 illustrates that a dispersive lens can also be used as focusing optics and the corresponding beam path of the interferometer measurement arm is shown in schematic form.

Finally, it should also be noted that a dispersive lens (709') can also be used as focusing optics (103, 319, 709). FIG. 10 shows a corresponding beam path of the interferometer measurement arm. The virtual focus 728 now occurs in place of the real focus 728.

Figure 11:
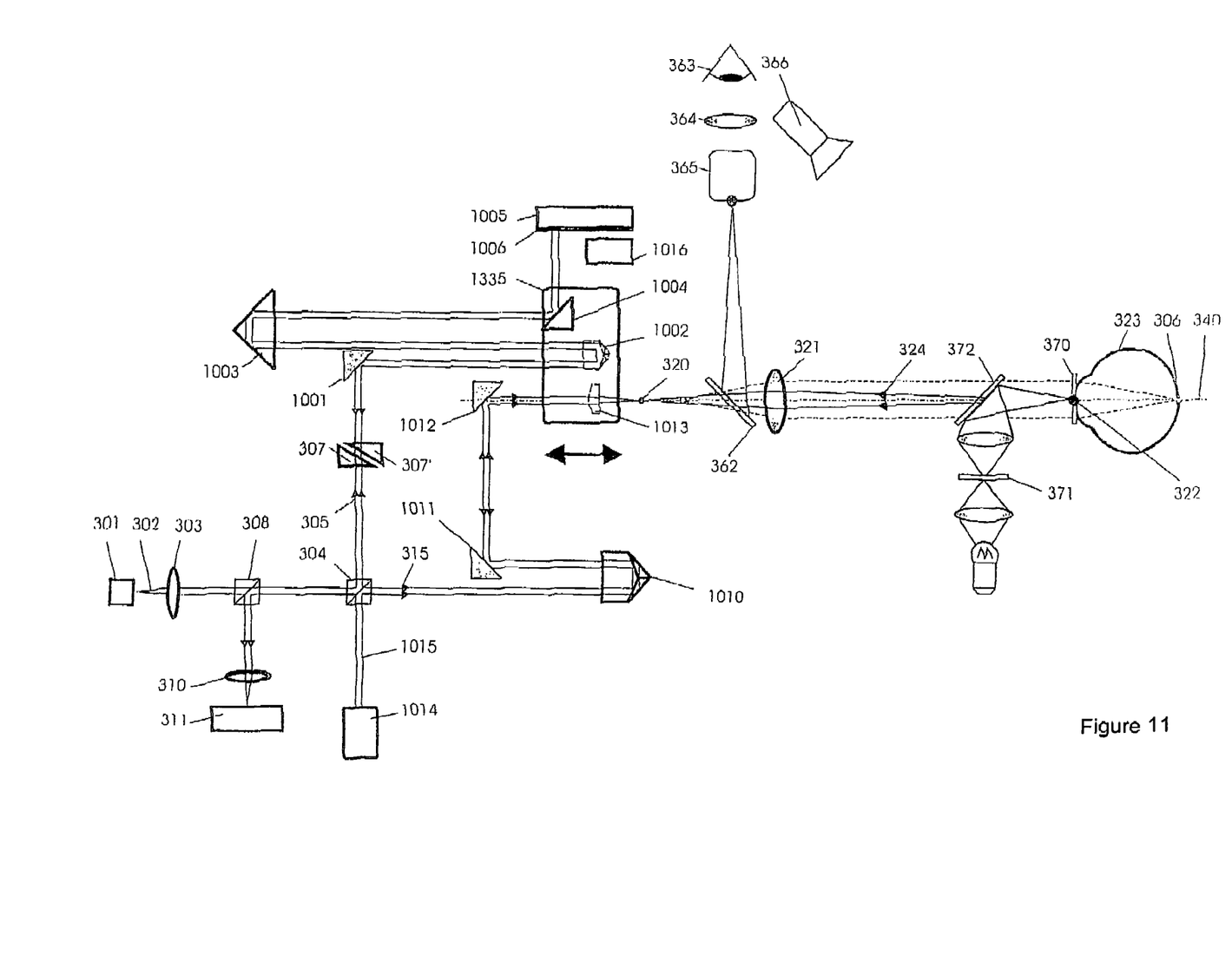
FIG. 11 illustrates a further embodiment of the invention in schematic form.

FIG. 11 shows another arrangement according to the invention. This arrangement makes it possible to use scanners with smaller scan travel by folding the reference beam. In the arrangement shown in the drawing, the reference beam runs back and forth three times between the reflectors 1001, 1002, 1003, and 1004. This reduces the scanner travel by a factor of 3. A further reduction in the required scan travel can be achieved by additional reflectors.

The short-coherence light source 301, e.g., a superluminescent diode, emits a light beam 302 which is partially coherent temporally and, as far as possible, fully coherent spatially and which illuminates the beamsplitter 304 through beamsplitter 308 by means of optics 303. The beamsplitter 304 divides the light beam 302 into measurement beam 315 and reference beam 305. The reference beam 305 is optically folded by a series of mirrors and reflectors. After traversing the dispersion compensation prisms 307 and 307', the reference beam 305 is initially directed by the right-angle mirror 1001 to the retroreflector mirror 1002 and from the latter back to the reflector mirror 1003 which reflects the reference beam further to the right-angle mirror 1004. Finally, the right-angle mirror 1004 directs the reference beam 305 to the reference mirror 1005 with the mirror surface 1006. The reference beam that is reflected at the latter runs back through the optical folding and is directed from the beamsplitter 308 and optics 310 to the photodetector 311.

The measurement beam 315 transmitted by the beamsplitter 304 (at right in the drawing) is focused on the focusing optics 1013 by the retroreflector 1010 via the right-angle mirrors 1011 and 1012 and is then focused in focus 320 by the focusing optics 1013. The relay optics 321 image the focus 320 on the eye 323 at point 322. Point 322 is located on the cornea of the eye 232 whose length is to be measured, for example.

Optics 1013, 1002, and 1004 are mounted on a scanner plate 1335 which is movable in direction of the interferometer axis 340 shown in dash-dot lines. The scanner plate 1335 can be the moving slide of a voice coil scanner—made by the company Physik Instrumente, for example—or of an ultrasound piezo-scanning table or another corresponding device.

Further, an auxiliary laser 1014 is provided for adjustment purposes, e.g., a helium-neon laser, whose beam 1015 is reflected in via the beamsplitter 304. The plane plate 1016 serves for dispersion compensation for measurements in the depth of the eye 323.

The dual-beam arrangement can also be used for all arrangements with the known advantage that eye movements of the test subject can be compensated in a corresponding manner.

Figure 12:
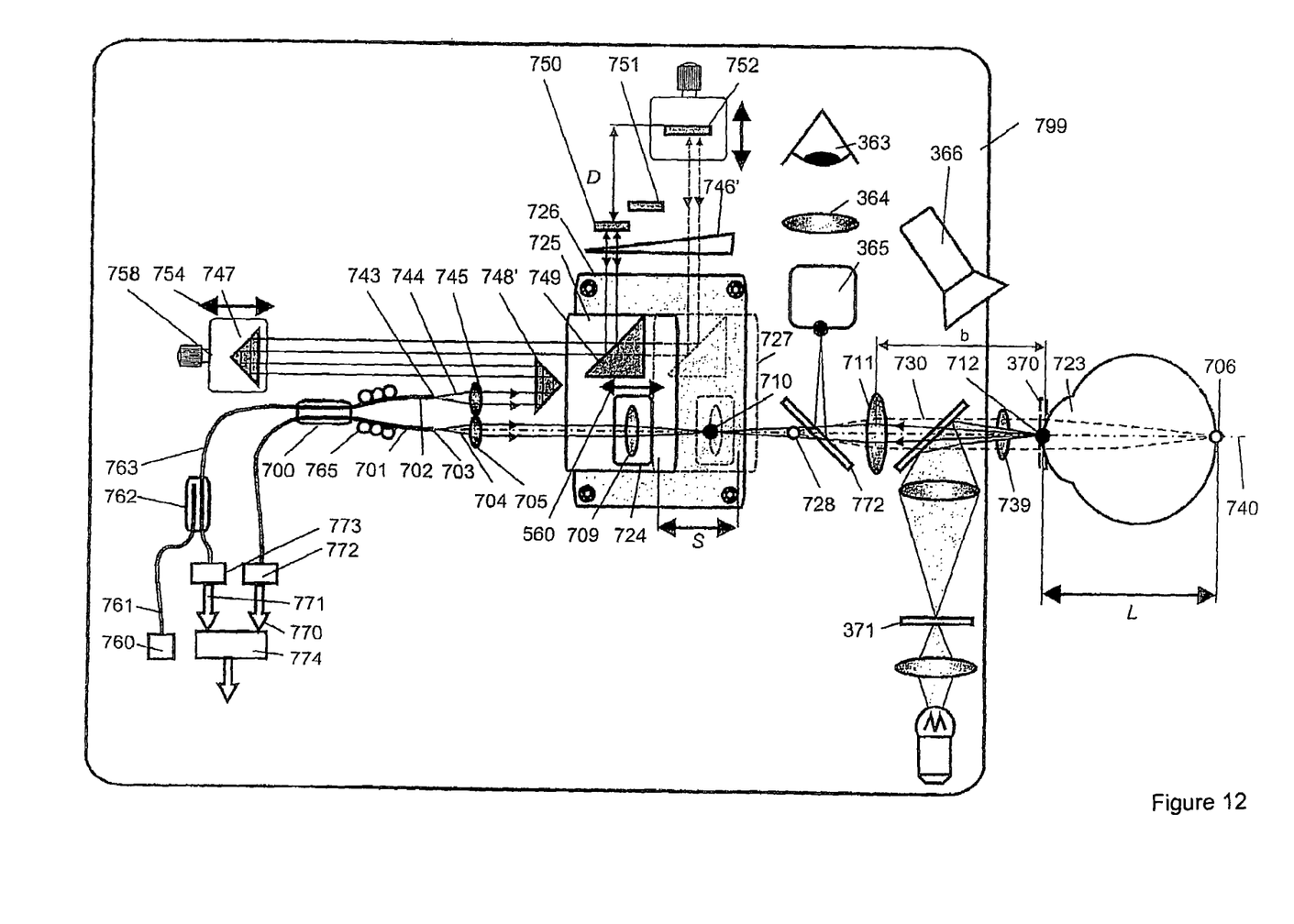
FIG. 12 shows a schematic arrangement in accordance with the invention where the dispersion compensation can be carried out by a wedge arrangement.

As is shown in the example in FIG. 12, the dispersion compensation can also be carried out by a wedge arrangement or prism arrangement 746 which is traversed depending on the displacement position of the scanning table. The beam deflections (not shown) which occur in this way must be taken into account in orienting the rest of the components (e.g., reference mirror).

Another advantageous arrangement consists in providing additional means which make it possible to carry out deliberate orientation of the optical axis of the device relative to the optical axis of the eye or visual axis, for example, by means of a method such as that described in PCT Application WO 2002/065899 A2, whose entire disclosure is hereby referenced, or through correspondingly adjustable beam deflecting elements (prisms, wedges) in the device itself.

While the foregoing description and drawings represent the present invention, it will be obvious to those skilled in the art that various changes may be made therein without departing from the true spirit and scope of the present invention.

The invention claimed is:

1. A short-coherence interferometer for measuring partial distances of an eye which focuses a measurement beam on a respective coherence window and/or reduces required interferometer mirror scan distances to distances that are less than distances which must be measured, comprising:
    at least one deflecting element with a deflecting angle $\alpha$; and
    elements of focusing optics in the short-coherence interferometer carrying out a periodic back-and-forth movement so that the measurement beam focus which is generated by the focusing optics and imaged on the eye by relay optics is moved synchronously with the coherence window from the cornea along the optic axis of the eye to the retina, and back;
    wherein at least one deflecting element moves to direct the measurement beam or a reference beam sequentially to a series of reflectors arranged in a staggered manner with respect to depth and/or laterally.

2. The short-coherence interferometer for measuring partial distances of the eye according to claim 1;
    wherein the position of the reflectors which are arranged in a staggered manner with respect to depth and laterally is adjustable and/or the positioning is carried out in an adaptive manner according to previously determined reference positions of the eye interfaces.

3. The short-coherence interferometer for measuring partial distances of the eye according to claim 1;
    wherein at least one deflecting element and the focusing optics are arranged one behind the other and/or next to one another in the movement direction on a table of a scanning device that is moved periodically back and forth.

4. The short-coherence interferometer for measuring partial distances of the eye according to claim 1;
    wherein at least one deflecting element and the focusing optics are arranged one behind the other and/or next to one another at a desired angle to the movement direction on a table of a scanning device that is moved periodically back and forth.

5. The short-coherence interferometer for measuring partial distances of the eye according to claim 1;
    wherein the measurement beam focus generated by the focusing optics is imaged on the eye by relay optics, wherein the corneal vertex is arranged exactly or approximately at a distance from the relay optics, where f is the focal length of the relay optics, L is the optical length of the eye, D is the distance of the reflectors associated with the cornea and fovea centralis.

6. The short-coherence interferometer for measuring partial distances of the eye according to claim 1;

wherein the measurement beam focus generated by the focusing optics is moved back and forth periodically by a distance somewhat greater than L–D (L=optical length of the eye; D=distance of the reflectors associated with the cornea and fovea centralis).

7. The short-coherence interferometer for measuring partial distances of the eye according to claim 1;
wherein the short-coherence interferometer is split into an interferometer measurement arm and a reference arm which is carried out by means of one or more fiber-optic couplers.

8. The short-coherence interferometer for measuring partial distances of the eye according to claim 1;
wherein at least one deflecting element and elements of the focusing optics are mounted next to one another in the movement direction or at an angle to the movement direction on separate scanning devices which are moved periodically back and forth.

9. The short-coherence interferometer for measuring partial distances of the eye according to claim 1;
wherein at least one deflecting element and elements of the focusing optics are mounted on separate scanning devices which are moved periodically back and forth, and the movements of the two scanning devices are electronically synchronized, or the movements can be modified in function relative to one another.

10. The short-coherence interferometer for measuring partial distances of the eye according to claim 3;
wherein the scanning device is a scanning table controlled by a stepper motor or piezo-motor, a voice coil scanner, or an ultrasound piezo-scanning table.

11. The short-coherence interferometer for measuring partial distances of the eye according to claim 1;
wherein a collecting lens, a dispersion lens or an optical system comprising a plurality of fixed or variable elements is used as focusing optics.

12. The short-coherence interferometer for measuring partial distances of the eye according to claim 7;
wherein a so-called rapid scan optical delay line or other path length modulator is also used with the interferometer in the reference arm or measurement arm.

13. The short-coherence interferometer for measuring partial distances of the eye according to claim 1;
wherein the initial coincidence of the measurement focus and coherence window is placed approximately in the center of the anterior chamber of the eye or at another desired location by additional means for adjusting an optical element in the beam path, e.g., by means of a mirror.

14. The short-coherence interferometer according to claim 13;
wherein the additional means for adjusting an optical element in the beam path is a mirror.

15. The short-coherence interferometer for measuring partial distances of the eye according to claim 1;
wherein the scan travel is reduced by optical folding of the reference beam path and/or measurement beam path.

16. The short-coherence interferometer for measuring partial distances of the eye according to claim 1;
wherein a dispersion compensation is carried out automatically by traversing wedge plates which are arranged in the reference beam path parallel to the movement direction, and the compensating action therefore depends on the displacement position.

17. The short-coherence interferometer for measuring partial distances of the eye according to claim 1;
wherein means are provided for adjusting or orienting the measurement beam axis relative to the optical axis or to the visual axis of the eye.

18. The short-coherence interferometer for measuring partial distances of the eye according to claim 1;
wherein a construction based on a dual beam method is used.

19. The short-coherence interferometer for measuring partial distances of the eye according to claim 1;
wherein a right-angle mirror or right-angle prism is provided as deflecting element.

* * * * *